(12) United States Patent
Venkatesh et al.

(10) Patent No.: US 6,936,459 B1
(45) Date of Patent: Aug. 30, 2005

(54) **MEDIUM FOR THE PRODUCTION OF BETACAROTENE AND OTHER CAROTENOIDS FROM *DUNALIELLA SALINA* (ARL 5) AND A STRAIN OF *DUNALIELLA SALINA* FOR PRODUCTION OF CAROTENES USING THE NOVEL MEDIA**

(75) Inventors: Nidamangala Srinivasa Venkatesh, Tamil Nadu (IN); Rajagopal Balaji, Tamil Nadu (IN); Parthasarathy Satnyamurthy, Tamil Nadu (IN)

(73) Assignee: Proalgen Biotech Limited, Chennai (IN)

( * ) Notice: Subject to any disclaimer, the term of this patent is extended or adjusted under 35 U.S.C. 154(b) by 326 days.

(21) Appl. No.: 10/129,387

(22) PCT Filed: Nov. 9, 2000

(86) PCT No.: PCT/IN00/00108

§ 371 (c)(1),
(2), (4) Date: May 3, 2002

(87) PCT Pub. No.: WO01/34092

PCT Pub. Date: May 17, 2001

(30) Foreign Application Priority Data

Nov. 11, 1999 (IN) .................................. 1088/MAS/99

(51) Int. Cl.$^7$ .................................................. C12N 1/12
(52) U.S. Cl. ...................... 435/257.1; 435/946; 435/67; 424/195.17; 47/1.4
(58) Field of Search .............................. 435/257.1, 946, 435/67; 424/195.17; 47/1.4

(56) References Cited

U.S. PATENT DOCUMENTS

| | | | | |
|---|---|---|---|---|
| 4,115,949 A | * | 9/1978 | Avron et al. ................... | 47/1.4 |
| 4,554,390 A | * | 11/1985 | Curtain et al. ............... | 568/870 |
| 5,776,349 A | * | 7/1998 | Guelcher et al. ........... | 210/703 |

\* cited by examiner

*Primary Examiner*—Irene Marx
(74) *Attorney, Agent, or Firm*—Roylance Abrams Berdo & Goodman, L.L.P.

(57) ABSTRACT

The invention relates to the development of a novel medium starting from fresh water using a salt solution complex comprising a non conventional salt, namely KCl and conventional salts such as NaCl and MgSO$_4$ in the proportion defined in the specification to generate biomass of higher carotenogenesis in particular Betacarotene and its isomers using *Dunaliella salina* ARL5 in a single stage of active growth. *D.salina* ARL5, a local isolate, has an unique property of having a wide range of pH and temperature tolerance which is beneficial in production terms as it is grown in external conditions (i.e. outdoors).

24 Claims, 1 Drawing Sheet

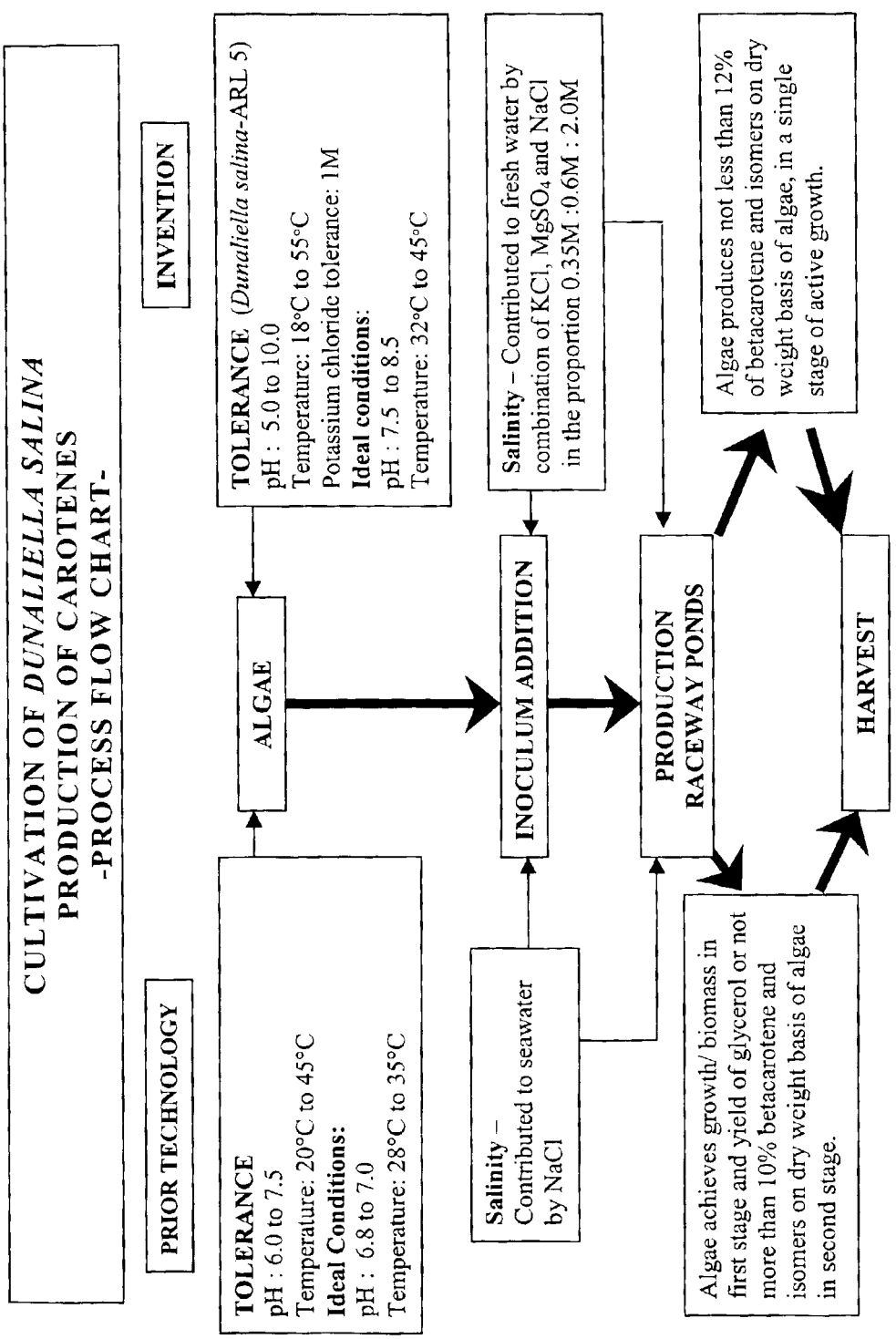

US 6,936,459 B1

MEDIUM FOR THE PRODUCTION OF BETACAROTENE AND OTHER CAROTENOIDS FROM *DUNALIELLA SALINA* (ARL 5) AND A STRAIN OF *DUNALIELLA SALINA* FOR PRODUCTION OF CAROTENES USING THE NOVEL MEDIA

This application was filed under 35 USC 371 as the national phase of PCT/IN00/00108 filed Nov. 9, 2000.

FIELD OF INVENTION

This invention in general relates to a novel medium using a salt solution complex in the specified proportion starting from fresh water for the production and maximization of Betacarotene and its isomers using an unique strain (ARL5) of the algae *Dunaliella salina* in a single stage of active growth.

This invention further relates to development of novel *Dunaliella salina* ARL5 strain using the said novel medium as hereinabove described. Further the invention relates to a process using the novel medium for producing betacarotene and other carotenoids using the said strain.

The following description in detail traces the various prior art technologies, methods or practices in respect of creation/development of media for the cultivation of *Dunaliella salina*. The description traces various patent specifications granted in respect of this field of technology and summarizes the information contained therein.

STATE OF THE PRIOR ART

*Dunaliella salina* belongs to the family *Chlorophycae* order *Volvocales*, being a unicellular motile green algae of the size ranging from 10–16 microns, the cells are broadly ovoid or ellipsoid in shape with a fine elastic periplast but with no rigid cell wall, two flagella 1.5 to 2 times the lengths of the cell emerge from one edge of the long cell axis, one large chloroplast occupies about half the nucleus, a single median pyrenoid is embedded in the basal portion of the chloroplast and surrounded by starch granules, the cells reproduce vegetatively by longitudinal division of the motile cells, the cells accumulate large quantities of carotenes (predominantly betacarotene and its isomers), providing as by-product a substance having a high protein content (biomass) and which can be utilised for various purposes such as a precursor for Vitamin A.

The U.S. Pat. No. 4,115,949 relates to a culture media developed from seawater for an algal species known as *Dunaliella* species. Cultivation of the algae, *Dunaliella salina* in mass scale has been reported in this patent using a seawater medium augmented to a sodium chloride content of 1M to 4M NaCl, about 1 to 20 mM potassium nitrate and preferably about 3 to 5 mM potassium nitrate, about 0.01 mM $KH_2PO_4$; about 0.5 $\mu M$ to 2 $\mu M$ $FeCl_3$-EDTA and preferably about 1 $\mu M$ to 2 $\mu M$ $FeCl_3$-EDTA. This patent also refers to substitution of potassium nitrate by ammonium nitrate and $KH_2PO_4$ by $NH_4H_2PO_4$ for satisfactory results.

The U.S. Pat. No. 4,958,460 relates to the method of growing and harvesting microorganisms like *Dunaliella* species. This patent refers to a medium starting with saline water from a lake, pond or ocean wherein the desired degree of salinity is established by addition of NaCl or fresh water or by evaporation to increase salinity to 15% to 25% as also the addition of the other normal nutrients. This patent also refers to growth of the algae i.e. biomass maximization in the first stage and yield maximization of the algae in the second stage by increasing salinity.

A Japanese patent (JP57159484) for the cultivation of *Dunaliella* species was also performed in hypertonic solution of sodium chloride with high concentration of Magnesium sulphate (0.3–1M).

In all these patents, the culturing media has been clearly defined for the production of betacarotene and its isomers, glycerol and single cell protein. It is also known that some of the genus of *Dunaliella* algae have a content of carotenes and carotene like substances and that these impart to such algae an orange to reddish-brown color. The content of carotenes produced is normally quite low and generally does not exceed about 4% by dry weight of biomass.

The U.S. Patents refer to addition of only NaCl to augment the salinity of the seawater medium and not potassium chloride and magnesium sulphate. Further these patents refer to a two stage process consisting distinctly of the first stage for growth and the second for yield maximization. The Japanese patent specifies the use of magnesium sulphate in addition to NaCl but does not specify potassium chloride.

The above patents generally cover growth of the algae of the *Dunaliella* species outdoors in ponds as also the common nutrients added to the medium for algal growth.

Cultivation of *Dunaliella salina* and production of carotenes using potassium chloride is thus not known in the art nor is mentioned in any of the patents.

As a substantial improvement to the specifications patented so far an attempt is made herein to prepare a novel artificial medium starting from fresh water and to use a salt solution complex comprising KCL, NaCl and $MgSO_4$ either independently or in every combination thereof to maximize the yield of betacarotene and its isomers and to obtain the said yield in a single stage of active growth. The very object of the invention is to evaluate exactly whether KCl can be used in the preparation of the artificial medium from fresh water and its effect on carotenogenesis wherein a very high yield of about 12% dry weight basis of betacarotene and its isomers can be obtained by a single stage process signifying simultaneous biomass maximization and carotenogenesis.

SUMMARY OF THE INVENTION

According to the invention, a new culturing media has been developed using a salt solution complex comprising: (a) potassium chloride as a key constituent contributing to salinity in addition to (b) a high concentration of sodium chloride and magnesium sulphate. *Dunaliella salina* ARL5 algae is grown in this media to produce and maximize betacarotene and its isomers in a single stage of active growth. This invention is unique in that *Dunaliella salina* ARL5, due to the constituents of the novel medium, exhibits biomass maximization or growth and carotenogensis simultaneously.

*Dunaliella salina* ARL5 was accepted for deposit with the Culture Collection of Algae and Protozoa (CCAP) at SAMS Research Services Ltd., OBAN, Argyll PA371QA, Scotland, UK under the Budapest Treaty and accorded accession no. CCAP 19/36 on 12 Nov. 2004.

Substituting NaCl with KCl as an artificial medium from fresh water did not support growth but in combination with sodium chloride and magnesium sulphate in the artificial medium from fresh water in a specific proportion, we have been very successful in the cultivation of *D. salins* ARL5 for the production of biomass, betacarotene and its isomers and the other carotenoids. The addition of KCl in this proportion has benefited not only by simultaneous growth and carotenogenesis but also by generating more betacarotene and its isomers i.e. 12% on dry weight basis as compared to 8 to 10% under conventional methods (two stage process), in a single stage of active growth.

The study also confirms that *Dunaliella salina* ARL5 has better properties as far as growth conditions are concerned than those reported to date. The characteristics of the strain ARL5 are that it tolerates a wide pH range from 5.0 to 10.0 pH and a temperature range of 18° C. to 55° C. The existing strains till date have a 6.0–7.5 pH range and a temperature range of 20° C. to 45° C. The study also confirms that the *D. saling* strain ARL5 also grows on salinity contributed by either sodium chloride or magnesium sulphate.

The advantages of this novel strain are that it can withstand a wide pH range and temperature shifts and also continue to grow (biomass) while generating betacarotene, other carotenoids and glycerol. The strain grows comfortably in artificial media from fresh water prepared using NaCl alone, NaCl and $MgSO_4$ combination as well as with NaCl+$MgSO_4$+KCl combination.

It has been a break through in the findings that use of potassium chloride as a single ingredient is toxic to the development of algae (*Dunaliella salina*) but use of potassium chloride in combination with other ingredients (contributing to salinity viz sodium chloride and magnesium sulphate) as invented by virtue of extensive research, results in an unexpectedly high yield of betacarotene and its isomers on a dry weight basis of algae.

Taking the various aspects of the invention together, the various objectives of the invention are stated herein under.

It is the primary object of the invention to construct/develop a novel medium from fresh water for cultivation of *Dunaliella salina* for the production and maximization of betacarotene and its isomers and other carotenoids in a single stage of active growth.

It is another object of the invention to develop a novel strain and a process medium for the cultivation of the novel strain of *Dunaliella salina* to produce betacarotene and its isomers and other carotenoids.

It is another object of the invention to use the novel strain of *Dunaliella salina* to produce carotenoids.

It is another object of the invention to use the novel strain of *Dunaliella salina* whole cells and or cell constituents as feed for crustaeceans and animals.

Further object of the invention will be clear from the ensuing description.

It is an embodiment of the invention that this invention leads to contrivance of novel medium starting from fresh water for the cultivation of *Dunaliella salina* The salinity is contributed by the addition of a salt solution complex comprising of a new chemical component i.e., potassium chloride to sodium chloride and magnesium sulphate, in a particular proportion as defined in the specification.

A novel medium for the cultivation of *Dunaliella salina* wherein the novel media being in the proportion of KCl 0.2M–1M, NaCl 1M–5M and $MgSO_4$ 0.41M–1.5M.

It is another embodiment of the invention that this novel medium for the cultivation of *Dunaliella salina* ARL5 wherein salinity is contributed by a proportion of KCl 0.2M–1M, preferably 0.35M; NaCl 1M–5 M, preferably 2M; $MgSO_4$ 0.41M–1.5M, preferably 0.6M and which comprises of other conventional nutrients as known to the art such as nitrates, phosphates, carbon (such as $CO_2$, $HCO_3$), iron delivered as chelate, magnesium, calcium and potassium.

It is another embodiment of the invention that for the cultivation of *Dunaliella salina* ARL5 wherein this novel medium induces the generation of a higher concentration of carotenoids in particular betacarotene and its isomers having a concentration of 10–12% on dry weight basis of biomass, as compared to the use of conventional method (use of sodium chloride) yield of 8–10% on dry weight basis.

It is another embodiment of the invention that this novel medium for the cultivation of *Dunaliella salina* ARL5 is an unique strain isolated from the coastline of Chennai, Tamil Nadu, India and which has a wide pH, temperature and potassium chloride, tolerance.

It is another embodiment of the invention that this new strain of *Dunaliella salina* has a pH range of 5.0–10.0 and a temperature range of 18° C.–55° C. and high potassium chloride tolerance from 0.2–1.0M.

It is another embodiment of the invention that *Dunaliella salina* ARL5 has a preferable range of 7.5–8.5 pH and a preferable temperature range of 32° C.–45° C.

BRIEF DESCRIPTION OF THE FIGURE

FIG. 1 is a comparison of the process for producing carotenes by the invention and by the prior technology.

DETAILED DESCRIPTION OF THE PREFERRED EMBODIMENT

The nature of the invention and the manner in which it is to be performed is clearly described in the specification. The invention has various components and they are clearly described in the following pages of complete specification.

Now the invention will be described in detail and specifically with reference to FIG. 1 contained in this complete specification.

The present invention provides a process for the cultivation of an algae designated by us as *Dunaliella salina* ARL5 (a local isolate of the Coast of Chennai, Tamilnadu, India), which belongs to the Class of Chlorophyceae, Order of *Volvocales*.

The algae used in the process of the present invention are unicellular motile cells. The cells are broadly ovoid or ellipsoid in shape with a fine elastic periplast but with no rigid cell wall and has two flagella of 1.5 to 2 times the length of the cell emerge from one edge of the long cell axis, one large chloroplast occupies about half the cell volume and is often arranged in a cup-shape around the nucleus. A single median pyrenoid is embedded in the basal portion of the chloroplast and surrounded by starch granules. These cells reproduce vegetatively by longitudinal division of the motile cells.

After extensive experiments, optimum conditions of cultivation have been defined with the use of KCl as a constituent of salinity in the novel medium from fresh water. This results in the desired production of large quantities of carotenoids, providing as by-product a substance having a high protein content which can be utilized for various purposes.

When grown outdoors under suitable illumination, the cells are bright orange and have a high carotene content, which can reach values as high as 120 mg per gram of dry weight of algae. Since the cultivation is done outdoors, the diurnal cycle is provided naturally.

A novel medium starting from fresh water ought to contain the following nutrients:

| Nutrient | Concentration Range | Preferred Range |
|---|---|---|
| KCl | 0.2–1 M | 0.35 M |
| NaCl | 1.0–5.0 M | 2.0 M |
| MgSO$_4$ | 0.41 M–1.5 M | 0.6 M |
| Ca$^{2+}$ | 0.01 mM–20 mM | 0.02 mM–0.04 mM |
| Iron source, such as FeEDTA | 0.5–4.5 µM | 1–3 µM |
| NO$_3{}^{2-}$ | 0.5–1.0 M | 0.5 mM |
| phosphate | 0.01 mM–1 mM | 0.5 mM |

A suitable source of carbon, such as HCO$^{3-}$ or CO$_2$ in growth medium as known to the art, is also provided.

The optimum pH for cultivation is between 7.5 and 8.5 and this is advantageously adjusted by adding required quantities of CO$_2$ through a pH controlled solenoid valve. The optimum temperature of cultivation is in the range of about 32–45° C.

Propagation of various contaminant microorganisms such as fungi, zooplankton, protozoans etc. is overcome to a very large extent due to the novel medium containing the salt solution complex comprising of high concentrations of potassium chloride (0.35M) with sodium chloride (2.0M) and magnesium sulphate (0.41M).

Optimization of the culture media (salinity and nutrient proportion) has been done to balance simultaneously growth (biomass) and production of betacarotene and its isomers (carotenogenesis). The carotenes are recovered from the algae and there remains a residue having a high protein content.

The novel process of cultivation on a predetermined culture medium from fresh water provides the possibility to obtain simultaneously two valuable products viz., (1) carotenes (betacarotene and its isomers and other carotenoids) and (2) algae meal. The high carotene content is a substantial improvement over processes used hitherto.

It is to be noted that the invention introduces a new paradigm concept leading to the simultaneous production of carotenes along with growth/ biomass has wide ramifications in view of extensive application in various fields of technology and industry, nevertheless specific use of invention is listed for perusal.

It is to be noted that the very objective of the description of the invention is to indicate salient features of the invention. It is to be further noted that this description is in no way to abridge the scope of the invention. Further, it is clear that within the scope of the invention various modifications are permissible. This scope of the invention is appended in the ensuing description.

In FIG. 1, the conventional route for the cultivation of *Dunaliella salina* and producing various carotenes and the route according to the invention is illustrated. Various steps involving the production of carotenes in both the routes are clearly illustrated On perusal of the FIG. 1, the differences are very clear.

The media used in the conventional process and the novel process are different. In the conventional process, seawater is augmented by sodium chloride for salinity while in the novel process, a salt solution complex comprising of a specified proportion of potassium chloride, magnesium sulphate and sodium chloride, contribute to salinity.

The algal strain, ARL5 and the novel medium constitute the subject matter of our invention. A comparison is made between the conventional process and our novel process in respect of the *D. salins* ARL5 strain in terms of parameters namely pH, temperature and the novel media tolerance:

pH range tolerance:
Existing strains of *Dunaliella salina*—6.5–8.0
Novel *Dunaliella salina* ARL5—5.0–10.0
Temperature Tolerance:
Existing strains *Dunaliella salina*—20° C. –45° C.
Novel *Dunaliella salina* ARL5—18° C.–55° C.
Novel Media Tolerance
Existing strains of *Dunaliella salina*—Presence of potassium chloride in the medium causes death.
Novel *Dunaliella salina* ARL5—High tolerance to potassium chloride (up to 1.0M)

EXAMPLE

Cultivation of *Dunalliella salina* ARL5 for Carotene Production.

*Dunaliella salina* ARL5 grown in a medium starting from fresh water augmented by a salt solution complex containing KCl 0.35M; NaCl 2.0M; MgSO$_4$ 0.6M, and with the addition of other ingredients comprise Ca$^{++}$, 0.04 mM; Iron source such as FeEDTA 3.0 µM; NO$_3{}^{2-}$(as potassium nitrate) 0.5 mM; phosphate (as potassium hydrogen ortho phosphate) 0.5 mM. CO$_2$ as carbon source is added by demand via a pH controlled solenoid valve. The pH is maintained automatically at pH 7.5–8.2 by adding CO$_2$ on demand. The algae are grown outdoors in 15 cm depth open raceway ponds under natural conditions of solar irradiation and temperature. The culture is kept under constant agitation using a paddle wheel agitator at about 20 rpm for about 8 hours a day.

*Dunaliella salina* ARL5 grow at a rate of 0.5–1.0 division per day and is harvested when the cells attain the biomass in the media that is measured using a spectrophotometer.

Cultures are harvested by flocculation using alum or ferric chloride followed by addition of a polyelectrolyte (food grade). Compressed air is sparged through the medium and the algae are allowed to stand for 30 min. The algae float on top of the media and are harvested. The media is returned to the pond. The cells thus harvested are transferred to the kettle and extracted in vegetable oil directly.

We claim:

1. A process for culturing *Dunaliella salina* ARL5 (CCAP 19/36) to produce algae cells having betacarotene and its isomers as well as a a high protein biomass by (a) growing *Dunaliella salina* ARL5 in an aqueous medium comprising: a salt solution complex comprising KCl, MgSO$_4$ and NaCl wherein the salt solution complex comprises 0.2M–1M KCl, 0.41M–1.5M MgSO$_4$, 1M–5M NaCl; and (b) recovering carotenes from said algae cells.

2. The process according to claim 1 wherein the salt solution complex comprises 0.35M KCl, 0.6M MgSO$_4$ and 2M NaCl.

3. The Process according to claim 1 wherein the culturing is allowed to proceed to a yield of not less than 12% betacarotene and its isomers on dry weight basis of said algae cells.

4. The process according to claim 1 further comprising recovering said biomass as an algae meal.

5. The process according to claim 1 wherein said salt solution complex further comprises: 0.01–20 mM Ca$^{2+}$.

6. The process according to claim 1 wherein said salt solution complex further comprises FeEDTA.

7. The process according to claim 1 wherein said salt solution complex further comprises: 0.5–5 M NO$_3{}^{2-}$.

8. The process according to claim 1 wherein said salt solution complex further comprises phosphate.

9. The process according to claim 8 wherein said phosphate is present in a concentration within the range of 0.01–1 mM.

10. The process according to claim 1 wherein said aqueous media exhibits a pH within the range of 7.5 and 8.5.

11. The process according to claim 10 wherein pH is controlled by adding carbon dioxide gas through a valve actuated according to measurement of pH of said aqueous media.

12. The process according to claim 1 wherein the temperature during the culturing step is within a range from about 32–45° C.

13. The process for culturing *Dunaliella salina* ARL5 (CCAP 19/36) to produce algae cell biomass comprising betacarotene and its isomers by (a) growing *Dunaliella salina* ARL5 in an aqueous media comprising: a salt solution complex comprising KCl, $MgSO_4$ and NaCl wherein the salt solution complex comprises 0.2M–1M KCl, 0.41M–1.5M $MgSO_4$, and 1M–5M NaCl; and (b) recovering said biomass.

14. A biologically pure culture of *Dunaliella salina* ARL5 (CCAP Accession no. 19/36) that resists to KCl at a concentration of up to 1M concentration.

15. The process for recovering *Dunaliella salina* ARL5 of claim 14 from admixture with other *Dunaliella salina* by contacting an aqueous medium comprising mixed strains of *Dunaliella salina* to potassium chloride at a concentration of up to 1 M KCl, at a pH within the range of 5.0 to 10.0 and a temperature within the range of 18° to 55° C. and recovering living *Dunaliella salina* ARL5.

16. The process according to claim 15 wherein said potassium chloride is present at a concentration within the range of 0.2–1.0 M.

17. A process for the production and maximization of natural beta-carotene and its isomers by:

cultivating strain *Dunaliella salina* ARL5 in a nutrient medium containing mineral requirements for growth of the algae until maximum desired concentration of algae is obtained, said nutrient medium comprising a salt solution complex comprising KCl, $MgSO_4$, and NaCl and having a concentration of each that is not greater than 1M KCl, 1.5M $MgSO_4$ and 5 M NaCl, harvesting the algae, recovering mixed carotenoids containing beta-carotene and its isomers in a concentration of not less than 70% purity from the harvested algae.

18. The process according to clam 17, wherein cultivating conditions are sufficient to produce beta-carotene and algae growth simultaneously.

19. The process according to claim 17 wherein said nutrient medium contains about 0.01 mM to 20 mM $Ca^{+2}$, 0.5 to 4.5 $\mu$M FeEDTA, 0.5 to 1 M $NO^{3-}$, and 0.01 to 1 mM $PO^{4-}$.

20. The process as according to claim 17, wherein harvesting the algae comprises flocculation.

21. The process according to claim 17, wherein harvesting the algae further comprises concentrating said algae using polyelectrolytes and forth flotation using compressed air.

22. The process according to claim 21, wherein the recovering step comprises:

contacting the concentrated algae under extraction conditions with an edible oil under nitrogen atmosphere to obtain a product oil containing mixed carotenoids that comprise beta-carotene and its isomers.

23. The process according to claim 22 wherein the recovering step further comprises:

allowing said product oil to stand at room temperature and filtering said product oil under vacuum to obtain a solid product comprising mixed carotenoid crystals containing not less than 70% beta-carotene.

24. A biologically pure culture of *Dunaliella salina* ARL 5 that has a pH tolerance within the range of 5–10, a temperature tolerance within the range of 18° to 55° C., and tolerates to KCl at a concentration of up to 1M.

* * * * *